(12) United States Patent
Minas et al.

(10) Patent No.: US 12,343,202 B2
(45) Date of Patent: Jul. 1, 2025

(54) STANDALONE FLEX CIRCUIT FOR INTRAVASCULAR IMAGING DEVICE AND ASSOCIATED DEVICES, SYSTEMS, AND METHODS

(71) Applicant: PHILIPS IMAGE GUIDED THERAPY CORPORATION, San Diego, CA (US)

(72) Inventors: Maritess Minas, San Diego, CA (US); Princeton Saroha, Ladera Ranch, CA (US); Jeremy Stigall, Carlsbad, CA (US); David Kenneth Wrolstad, Fallbrook, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 0 days.

(21) Appl. No.: 18/581,526

(22) Filed: Feb. 20, 2024

(65) Prior Publication Data

US 2024/0188929 A1   Jun. 13, 2024

Related U.S. Application Data

(63) Continuation of application No. 17/948,155, filed on Sep. 19, 2022, now Pat. No. 11,903,759, which is a
(Continued)

(51) Int. Cl.
*A61B 8/12* (2006.01)
*A61B 8/00* (2006.01)
*B06B 1/06* (2006.01)

(52) U.S. Cl.
CPC ............... *A61B 8/12* (2013.01); *A61B 8/445* (2013.01); *A61B 8/4483* (2013.01); *A61B 8/54* (2013.01);
(Continued)

(58) Field of Classification Search
CPC . A61B 8/12; A61B 17/2202; A61B 2562/164; A61B 2562/166; A61B 8/445;
(Continued)

(56) References Cited

U.S. PATENT DOCUMENTS 6,110,314 A    8/2000  Nix
6,641,540 B2  11/2003  Fleischman
(Continued)

FOREIGN PATENT DOCUMENTS

WO      2009073752 A1    6/2009

*Primary Examiner* — Mark D Remaly

(57) ABSTRACT

An intravascular imaging device is provided. In some embodiments, the intravascular imaging device includes a flexible elongate member sized and shaped for insertion into a vessel of a patient, the flexible elongate member having a proximal portion and a distal portion; and an imaging assembly disposed at the distal portion of the flexible elongate member, the imaging assembly including a flex circuit positioned directly around the flexible elongate member. In some embodiments, a method of assembling an intravascular imaging device includes obtaining a flex circuit including a first layer having a plurality of transducers and a second layer having an acoustic backing material; and positioning the flex circuit directly around a distal portion of a flexible elongate member.

11 Claims, 7 Drawing Sheets

Related U.S. Application Data continuation of application No. 16/088,161, filed as application No. PCT/EP2017/057562 on Mar. 30, 2017, now Pat. No. 11,446,000.

(60) Provisional application No. 62/315,416, filed on Mar. 30, 2016.

(52) U.S. Cl.
CPC ...... *B06B 1/0633* (2013.01); *A61B 2562/164* (2013.01); *A61B 2562/166* (2013.01)

(58) Field of Classification Search
CPC ....... A61B 8/4483; A61B 8/4488; A61B 8/54; B06B 1/0633; H05K 1/189; H05K 2201/10151; Y10T 156/1038; Y10T 156/1092; Y10T 156/1093; Y10T 29/42
See application file for complete search history.

(56) References Cited

U.S. PATENT DOCUMENTS

| | | |
|---|---|---|
| 6,776,763 B2 | 8/2004 | Nix |
| 7,226,417 B1 | 6/2007 | Eberle |
| 7,846,101 B2 | 12/2010 | Eberle |
| 10,555,720 B2 | 2/2020 | Corl |
| 11,160,529 B2 | 11/2021 | Wrolstad |
| 11,224,407 B2 | 1/2022 | Wrolstad |
| 2016/0029999 A1 | 2/2016 | Corl |
| 2019/0090843 A1 | 3/2019 | Saroha |
| 2020/0397403 A1 | 12/2020 | Minas |

STANDALONE FLEX CIRCUIT FOR INTRAVASCULAR IMAGING DEVICE AND ASSOCIATED DEVICES, SYSTEMS, AND METHODS

CROSS-REFERENCE TO PRIOR APPLICATIONS

This application is a continuation of U.S. application Ser. No. 17/948,155, filed Sep. 19, 2022, now U.S. Pat. No. 11,903,759, which is a continuation of U.S. application Ser. No. 16/088,161, filed on Sep. 25, 2018, now U.S. Pat. No. 11,446,000, which is the U.S. National Phase application under 35 U.S.C. § 371 of International Application No. PCT/EP2017/057562, filed on Mar. 30, 2017, which claims the benefit of Provisional Application Ser. No. 62/315,416, filed Mar. 30, 2016. These applications are hereby incorporated by reference herein.

TECHNICAL FIELD

The present disclosure relates generally to intravascular ultrasound (IVUS) imaging and, in particular, to the structure of an intravascular imaging device. For example, the structure can include a distal support member having a conductive portion that facilitates communication of electrical signals between a conductor and a flex circuit of the intravascular imaging device.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

Solid-state (also known as synthetic-aperture) IVUS catheters are one of the two types of IVUS devices commonly used today, the other type being the rotational IVUS catheter. Solid-state IVUS catheters carry a scanner assembly that includes an array of ultrasound transducers distributed around its circumference along with one or more integrated circuit controller chips mounted adjacent to the transducer array. The controllers select individual transducer elements (or groups of elements) for transmitting an ultrasound pulse and for receiving the ultrasound echo signal. By stepping through a sequence of transmit-receive pairs, the solid-state IVUS system can synthesize the effect of a mechanically scanned ultrasound transducer but without moving parts (hence the solid-state designation). Since there is no rotating mechanical element, the transducer array can be placed in direct contact with the blood and vessel tissue with minimal risk of vessel trauma. Furthermore, because there is no rotating element, the electrical interface is simplified. The solid-state scanner can be wired directly to the imaging system with a simple electrical cable and a standard detachable electrical connector, rather than the complex rotating electrical interface required for a rotational IVUS device.

Manufacturing an intravascular imaging device that can efficiently traverse physiology within the human body is challenging. In that regard, components at the distal portion of the imaging device causes an area of high rigidity in the intravascular device, which increase the likelihood of kinking as the intravascular is steered through vasculature.

Thus, there remains a need for intravascular ultrasound imaging system that overcomes the limitations of a rigid imaging assembly while achieving efficient assembly and operation.

SUMMARY

Embodiments of the present disclosure provide an improved intravascular ultrasound imaging system for generating images of a blood vessel. A distal portion of an intravascular imaging device can include a flex circuit. Whereas other imaging assemblies typically positioned the flex circuit around a rigid support structure, imaging assemblies of the present disclosure wrap the flex circuit directly around a flexible elongate member that extends along the length of the intravascular device. The flex circuit includes a plurality of transducers and a layer including acoustic backing material that facilitates operation of the transducers. By omitting the rigid support structure, imaging assemblies of the present disclosure are advantageously more flexible.

In one embodiment, an intravascular imaging device is provided. The intravascular imaging device includes a flexible elongate member sized and shaped for insertion into a vessel of a patient, the flexible elongate member having a proximal portion and a distal portion; and an imaging assembly disposed at the distal portion of the flexible elongate member, the imaging assembly including a flex circuit positioned directly around the flexible elongate member.

In some embodiments, the flex circuit comprises first layer having a plurality of transducers and a second layer having an acoustic backing material. In some embodiments, the first layer is positioned over the second layer. In some embodiments, the acoustic backing material comprises at least one of cerium oxide, an epoxy, tungsten, polymethylpentene, or crosslinked polystyrene. In some embodiments, the flex circuit further comprises a third layer comprising a first flexible substrate. In some embodiments, the third layer is positioned over the first layer. In some embodiments, the device further includes a fourth layer comprising a second flexible substrate. In some embodiments, the second layer is positioned over the fourth layer. In some embodiments, the flex circuit further comprises a plurality of controllers in communication with the plurality of transducers. In some embodiments, the flexible elongate member comprises an outer member and an inner member. In some embodiments, the flex circuit is positioned directly around the outer member.

In one embodiment, a method of assembling an intravascular imaging device is provided. The method includes obtaining a flex circuit including a first layer having a plurality of transducers and a second layer having an acoustic backing material; and positioning the flex circuit directly around a distal portion of a flexible elongate member.

In some embodiments, the obtaining includes forming the flex circuit such that the first layer is positioned over the second layer. In some embodiments, the forming further includes depositing the acoustic backing material over a first flexible substrate. In some embodiments, the acoustic backing material comprises at least one of cerium oxide, an epoxy, tungsten, polymethylpentene, or crosslinked polystyrene. In some embodiments, the forming further includes positioning a second flexible substrate over the first layer. In some embodiments, the flex circuit further includes a plurality of controllers in communication with the plurality of transducers. In some embodiments, the flexible elongate member comprises an inner member and an outer member, and wherein flex circuit is positioned directly around the outer member. In some embodiments, the method further includes coupling a distal member to at least one of the flex circuit or the flexible elongate member.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
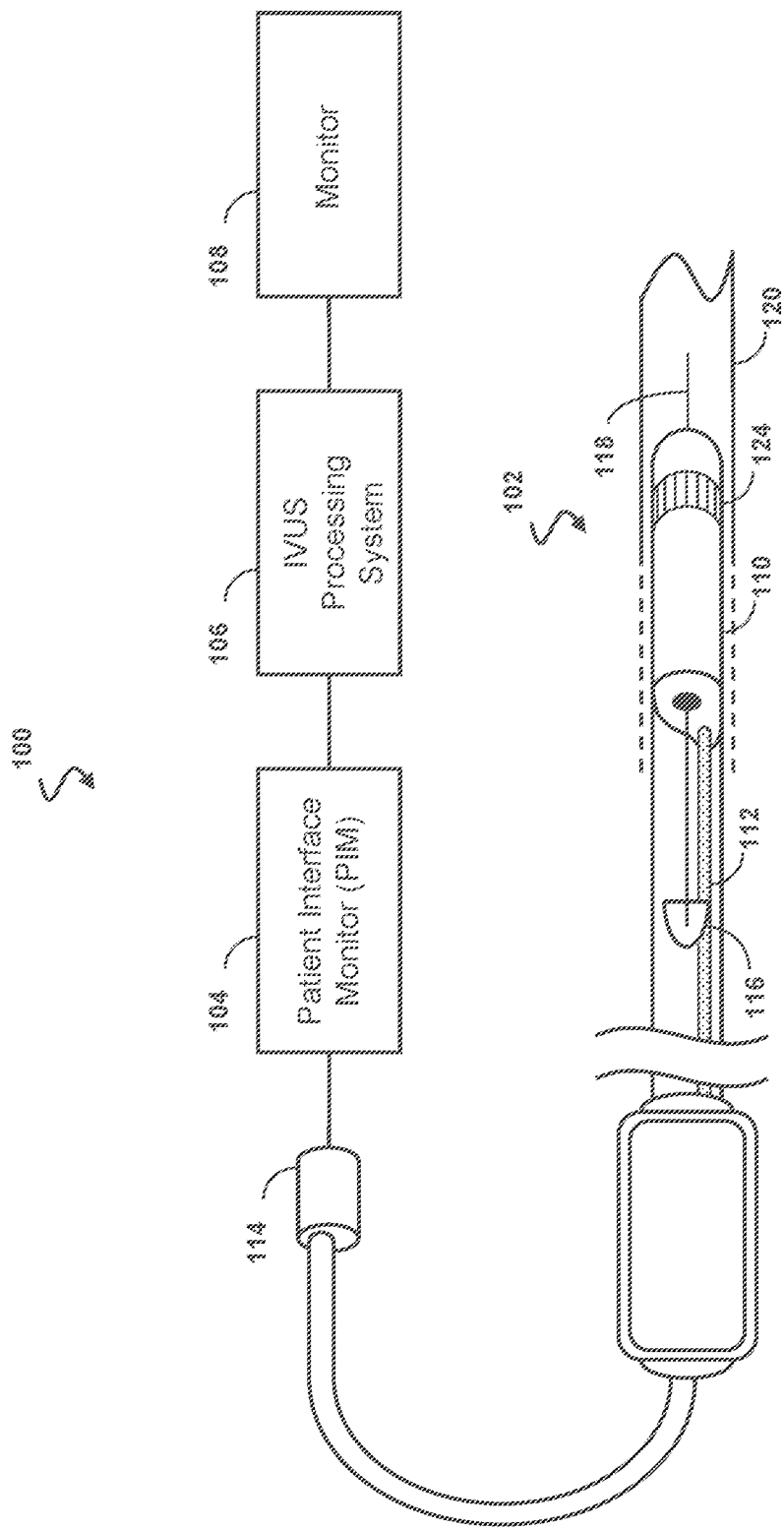
FIG. 1 is a diagrammatic schematic view of an imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the focusing system is described in terms of cardiovascular imaging, it is understood that it is not intended to be limited to this application. The system is equally well suited to any application requiring imaging within a confined cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an intravascular ultrasound (IVUS) imaging system 100, according to aspects of the present disclosure. The IVUS imaging system 100 may include a solid-state IVUS device 102 such as a catheter, guide wire, or guide catheter, a patient interface module (PIM) 104, an IVUS processing system or console 106, and a monitor 108.

At a high level, the IVUS device 102 emits ultrasonic energy from a transducer array 124 included in scanner assembly 110 mounted near a distal end of the catheter device. The ultrasonic energy is reflected by tissue structures in the medium, such as a vessel 120, surrounding the scanner assembly 110, and the ultrasound echo signals are received by the transducer array 124. The PIM 104 transfers the received echo signals to the console or computer 106 where the ultrasound image (including the flow information) is reconstructed and displayed on the monitor 108. The console or computer 106 can include a processor and a memory. The computer or computing device 106 can be operable to facilitate the features of the IVUS imaging system 100 described herein. For example, the processor can execute computer readable instructions stored on the non-transitory tangible computer readable medium.

The PIM 104 facilitates communication of signals between the IVUS console 106 and the scanner assembly 110 included in the IVUS device 102. This communication includes the steps of: (1) providing commands to integrated circuit controller chip(s) 206A, 206B, illustrated in FIG. 2, included in the scanner assembly 110 to select the particular transducer array element(s) to be used for transmit and receive, (2) providing the transmit trigger signals to the integrated circuit controller chip(s) 206A, 206B included in the scanner assembly 110 to activate the transmitter circuitry to generate an electrical pulse to excite the selected transducer array element(s), and/or (3) accepting amplified echo signals received from the selected transducer array element(s) via amplifiers included on the integrated circuit controller chip(s)126 of the scanner assembly 110. In some embodiments, the PIM 104 performs preliminary processing of the echo data prior to relaying the data to the console 106. In examples of such embodiments, the PIM 104 performs amplification, filtering, and/or aggregating of the data. In an embodiment, the PIM 104 also supplies high- and low-voltage DC power to support operation of the device 102 including circuitry within the scanner assembly 110.

The IVUS console 106 receives the echo data from the scanner assembly 110 by way of the PIM 104 and processes the data to reconstruct an image of the tissue structures in the medium surrounding the scanner assembly 110. The console 106 outputs image data such that an image of the vessel 120, such as a cross-sectional image of the vessel 120, is displayed on the monitor 108. Vessel 120 may represent fluid filled or surrounded structures, both natural and man-made. The vessel 120 may be within a body of a patient. The vessel 120 may be a blood vessel, as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be may be used to examine man-made structures such as, but without limitation, heart valves, stents, shunts, filters and other devices.

Figure 2:
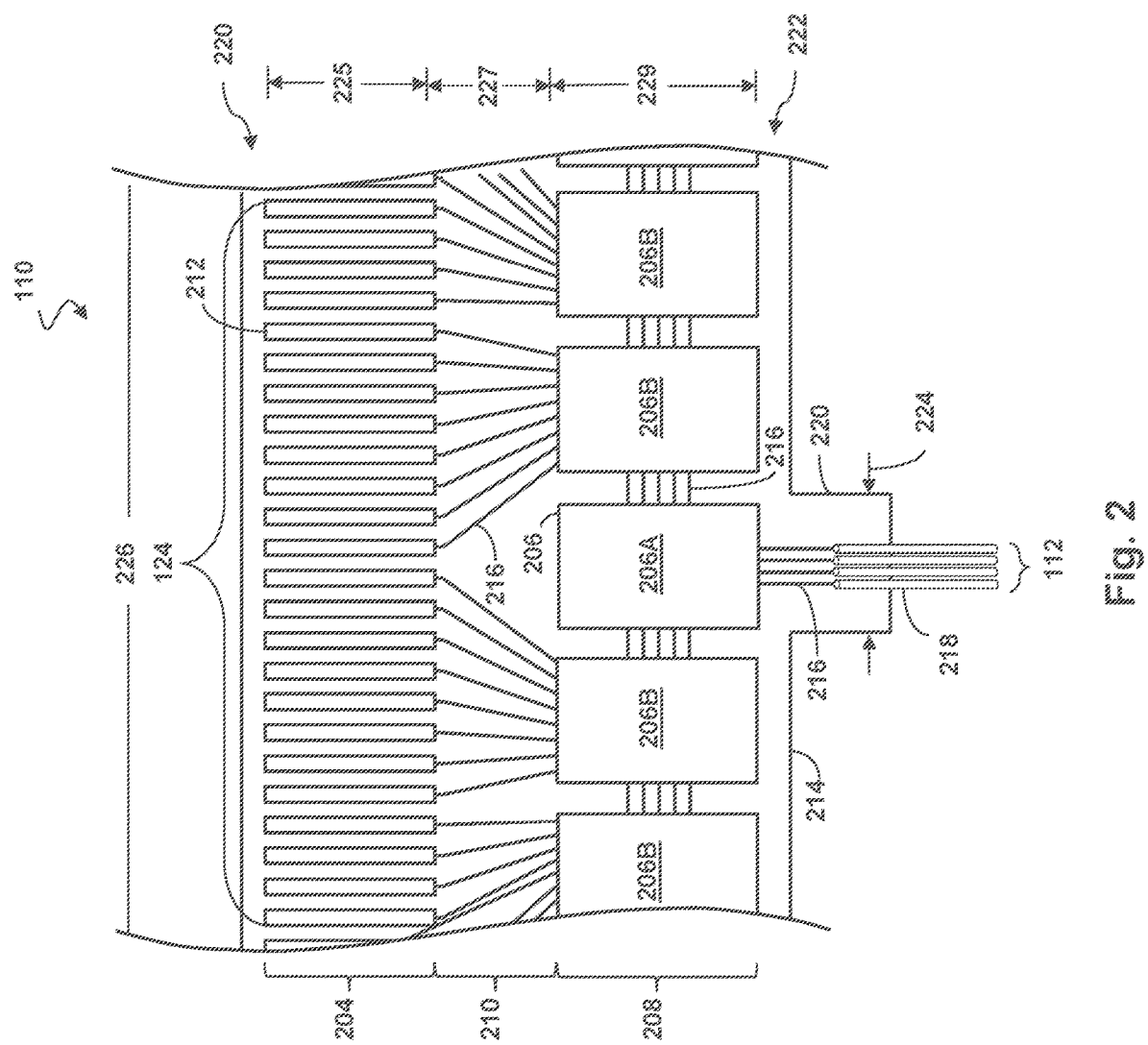
FIG. 2 is a diagrammatic top view of a scanner assembly in a flat configuration, according to aspects of the present disclosure.

In some embodiments, the IVUS device includes some features similar to traditional solid-state IVUS catheters, such as the EagleEye® catheter available from Volcano Corporation and those disclosed in U.S. Pat. No. 7,846,101 hereby incorporated by reference in its entirety. For example, the IVUS device 102 includes the scanner assembly 110 near a distal end of the device 102 and a transmission line bundle 112 extending along the longitudinal body of the device 102. The transmission line bundle or cable 112 can include a plurality of conductors, including one, two, three, four, five, six, seven, or more conductors 218 (FIG. 2). It is understood that any suitable gauge wire can be used for the conductors 218. In an embodiment, the cable 112 can include a four-conductor transmission line arrangement with, e.g., 41 AWG gauge wires. In an embodiment, the cable 112 can include a seven-conductor transmission line arrangement utilizing, e.g., 44 AWG gauge wires. In some embodiments, 43 AWG gauge wires can be used.

The transmission line bundle 112 terminates in a PIM connector 114 at a proximal end of the device 102. The PIM connector 114 electrically couples the transmission line bundle 112 to the PIM 104 and physically couples the IVUS device 102 to the PIM 104. In an embodiment, the IVUS device 102 further includes a guide wire exit port 116. Accordingly, in some instances the IVUS device is a rapid-exchange catheter. The guide wire exit port 116 allows a guide wire 118 to be inserted towards the distal end in order to direct the device 102 through the vessel 120.

Figure 3:
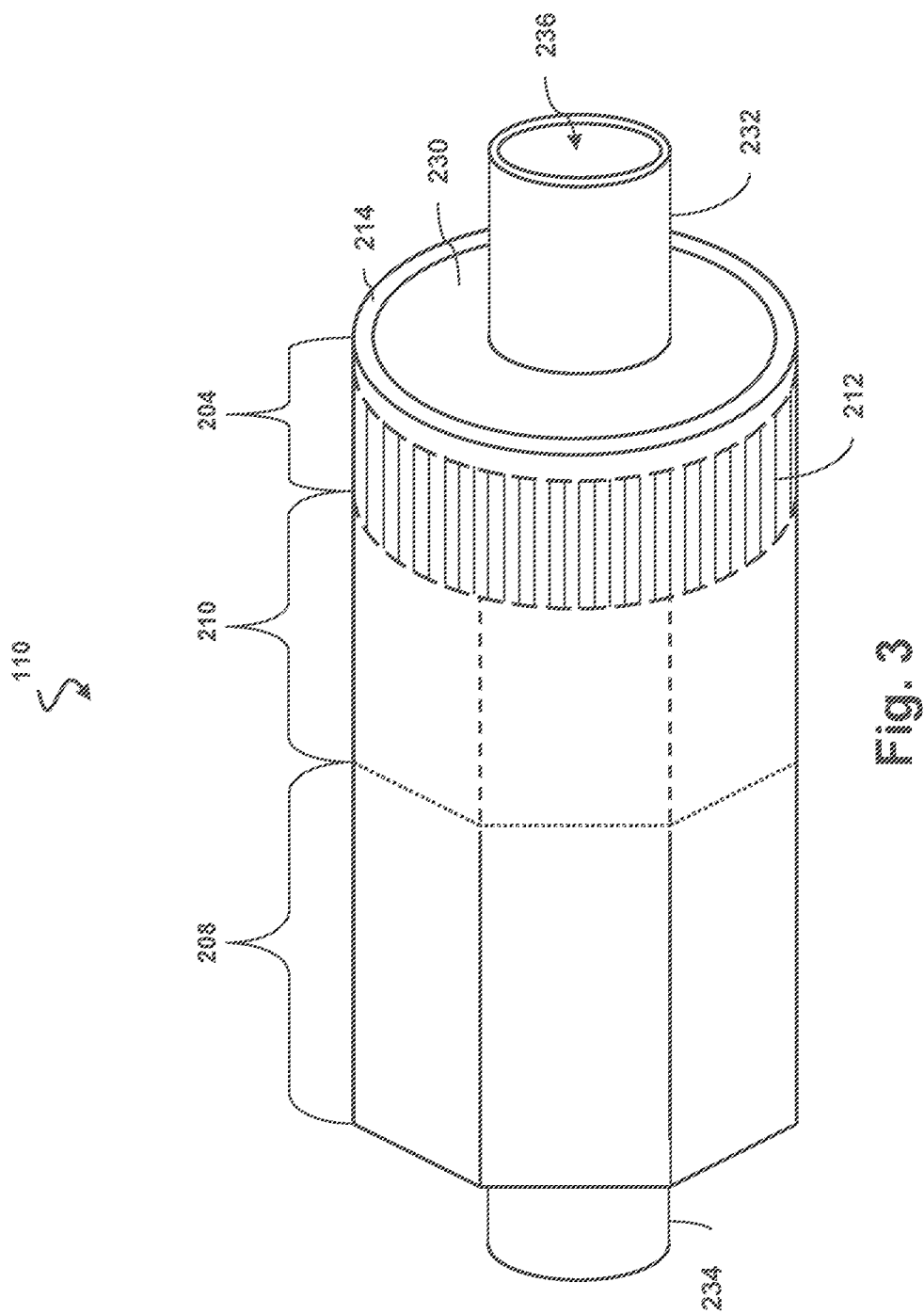
FIG. 3 is a diagrammatic side view of a scanner assembly in a rolled configuration around a support member, according to aspects of the present disclosure.

FIG. 2 is a top view of a portion of an ultrasound scanner assembly 110 according to an embodiment of the present disclosure. The assembly 110 includes a transducer array 124 formed in a transducer region 204 and transducer control logic dies 206 (including dies 206A and 206B) formed in a control region 208, with a transition region 210 disposed therebetween. The transducer control logic dies 206 and the transducers 212 are mounted on a flex circuit 214 that is shown in a flat configuration in FIG. 2. FIG. 3 illustrates a rolled configuration of the flex circuit 214. The transducer array 202 is a non-limiting example of a medical sensor element and/or a medical sensor element array. The transducer control logic dies 206 is a non-limiting example of a control circuit. The transducer region 204 is disposed adjacent a distal portion 220 of the flex circuit 214. The control region 208 is disposed adjacent the proximal portion 222 of the flex circuit 214. The transition region 210 is disposed between the control region 208 and the transducer region 204. Dimensions of the transducer region 204, the control region 208, and the transition region 210 (e.g., lengths 225, 227, 229) can vary in different embodiments. In some embodiments, the lengths 225, 227, 229 can be substantially similar or a length 227 of the transition region 210 can be greater than lengths 225, 229 of the transducer region and controller region, respectively. While the imaging assembly 110 is described as including a flex circuit, it is understood that the transducers and/or controllers may be arranged to form the imaging assembly 110 in other configurations, including those omitting a flex circuit.

The transducer array 124 may include any number and type of ultrasound transducers 212, although for clarity only a limited number of ultrasound transducers are illustrated in FIG. 2. In an embodiment, the transducer array 124 includes 64 individual ultrasound transducers 212. In a further embodiment, the transducer array 124 includes 32 ultrasound transducers 212. Other numbers are both contemplated and provided for. With respect to the types of transducers, in an embodiment, the ultrasound transducers 124 are piezoelectric micromachined ultrasound transducers (PMUTs) fabricated on a microelectromechanical system (MEMS) substrate using a polymer piezoelectric material, for example as disclosed in U.S. Pat. No. 6,641,540, which is hereby incorporated by reference in its entirety. In alternate embodiments, the transducer array includes piezoelectric zirconate transducers (PZT) transducers such as bulk PZT transducers, capacitive micromachined ultrasound transducers (cMUTs), single crystal piezoelectric materials, other suitable ultrasound transmitters and receivers, and/or combinations thereof.

The scanner assembly 110 may include various transducer control logic, which in the illustrated embodiment is divided into discrete control logic dies 206. In various examples, the control logic of the scanner assembly 110 performs: decoding control signals sent by the PIM 104 across the cable 112, driving one or more transducers 212 to emit an ultrasonic signal, selecting one or more transducers 212 to receive a reflected echo of the ultrasonic signal, amplifying a signal representing the received echo, and/or transmitting the signal to the PIM across the cable 112. In the illustrated embodiment, a scanner assembly 110 having 64 ultrasound transducers 212 divides the control logic across nine control logic dies 206, of which five are shown in FIG. 2. Designs incorporating other numbers of control logic dies 206 including 8, 9, 16, 17 and more are utilized in other embodiments. In general, the control logic dies 206 are characterized by the number of transducers they are capable of driving, and exemplary control logic dies 206 drive 4, 8, and/or 16 transducers.

The control logic dies are not necessarily homogenous. In some embodiments, a single controller is designated a master control logic die 206A and contains the communication interface for the cable 112. Accordingly, the master control circuit may include control logic that decodes control signals received over the cable 112, transmits control responses over the cable 112, amplifies echo signals, and/or transmits the echo signals over the cable 112. The remaining controllers are slave controllers 206B. The slave controllers 206B may include control logic that drives a transducer 212 to emit an ultrasonic signal and selects a transducer 212 to receive an echo. In the depicted embodiment, the master controller 206A does not directly control any transducers 212. In other embodiments, the master controller 206A drives the same number of transducers 212 as the slave controllers 206B or drives a reduced set of transducers 212 as compared to the slave controllers 206B. In an exemplary embodiment, a single master controller 206A and eight slave controllers 206B are provided with eight transducers assigned to each slave controller 206B.

The flex circuit 214, on which the transducer control logic dies 206 and the transducers 212 are mounted, provides structural support and interconnects for electrical coupling. The flex circuit 214 may be constructed to include a film layer of a flexible polyimide material such as KAPTON™ (trademark of DuPont). Other suitable materials include polyester films, polyimide films, polyethylene napthalate films, or polyetherimide films, other flexible printed semiconductor substrates as well as products such as Upilex® (registered trademark of Ube Industries) and TEFLON® (registered trademark of E.I. du Pont). In the flat configuration illustrated in FIG. 2, the flex circuit 214 has a generally rectangular shape. As shown and described herein, the flex circuit 214 is configured to be wrapped around a support member 230 (FIG. 3) to form a cylindrical toroid in some instances. Therefore, the thickness of the film layer of the flex circuit 214 is generally related to the degree of curvature in the final assembled scanner assembly 110. In some embodiments, the film layer is between 5 µm and 100 µm, with some particular embodiments being between 12.7 µm and 25.1 µm.

To electrically interconnect the control logic dies 206 and the transducers 212, in an embodiment, the flex circuit 214 further includes conductive traces 216 formed on the film layer that carry signals between the control logic dies 206 and the transducers 212. In particular, the conductive traces 216 providing communication between the control logic dies 206 and the transducers 212 extend along the flex circuit 214 within the transition region 210. In some instances, the conductive traces 216 can also facilitate electrical communication between the master controller 206A and the slave controllers 206B. The conductive traces 216 can also provide a set of conductive pads that contact the conductors 218 of cable 112 when the conductors 218 of the cable 112 are mechanically and electrically coupled to the flex circuit 214. Suitable materials for the conductive traces 216 include copper, gold, aluminum, silver, tantalum, nickel, and tin, and may be deposited on the flex circuit 214 by processes such as sputtering, plating, and etching. In an embodiment, the flex circuit 214 includes a chromium adhesion layer. The width and thickness of the conductive traces 216 are selected to provide proper conductivity and resilience when the flex circuit 214 is rolled. In that regard, an exemplary range for the thickness of a conductive trace 216 and/or conductive pad is between 10-50 µm. For example, in an embodiment, 20 µm conductive traces 216 are separated by 20 µm of space. The width of a conductive trace 216 on the flex circuit 214 may be further determined by the width of the conductor 218 to be coupled to the trace/pad.

The flex circuit 214 can include a conductor interface 220 in some embodiments. The conductor interface 220 can be a location of the flex circuit 214 where the conductors 218 of the cable 114 are coupled to the flex circuit 214. For example, the bare conductors of the cable 114 are electrically coupled to the flex circuit 214 at the conductor interface 220. The conductor interface 220 can be tab extending from the main body of flex circuit 214. In that regard, the main body of the flex circuit 214 can refer collectively to the transducer region 204, controller region 208, and the transition region 210. In the illustrated embodiment, the conductor interface 220 extends from the proximal portion 222 of the flex circuit 214. In other embodiments, the conductor interface 220 is positioned at other parts of the flex circuit 214, such as the distal portion 220, or the flex circuit 214 omits the conductor interface 220. A value of a dimension of the tab or conductor interface 220, such as a width 224, can be less than the value of a dimension of the main body of the flex circuit 214, such as a width 226. In some embodiments, the substrate forming the conductor interface 220 is made of the same material(s) and/or is similarly flexible as the flex circuit 214. In other embodiments, the conductor interface 220 is made of different materials and/or is comparatively more rigid than the flex circuit 214. For example, the conductor interface 220 can be made of a plastic, thermoplastic, polymer, hard polymer, etc., including polyoxymethylene (e.g., DELRIN®), polyether ether ketone (PEEK), nylon, and/or other suitable materials. As described in greater detail herein, the support member 230, the flex circuit 214, the conductor interface 220 and/or the conductor (s) 218 can be variously configured to facilitate efficient manufacturing and operation of the scanner assembly 110.

Figure 4:
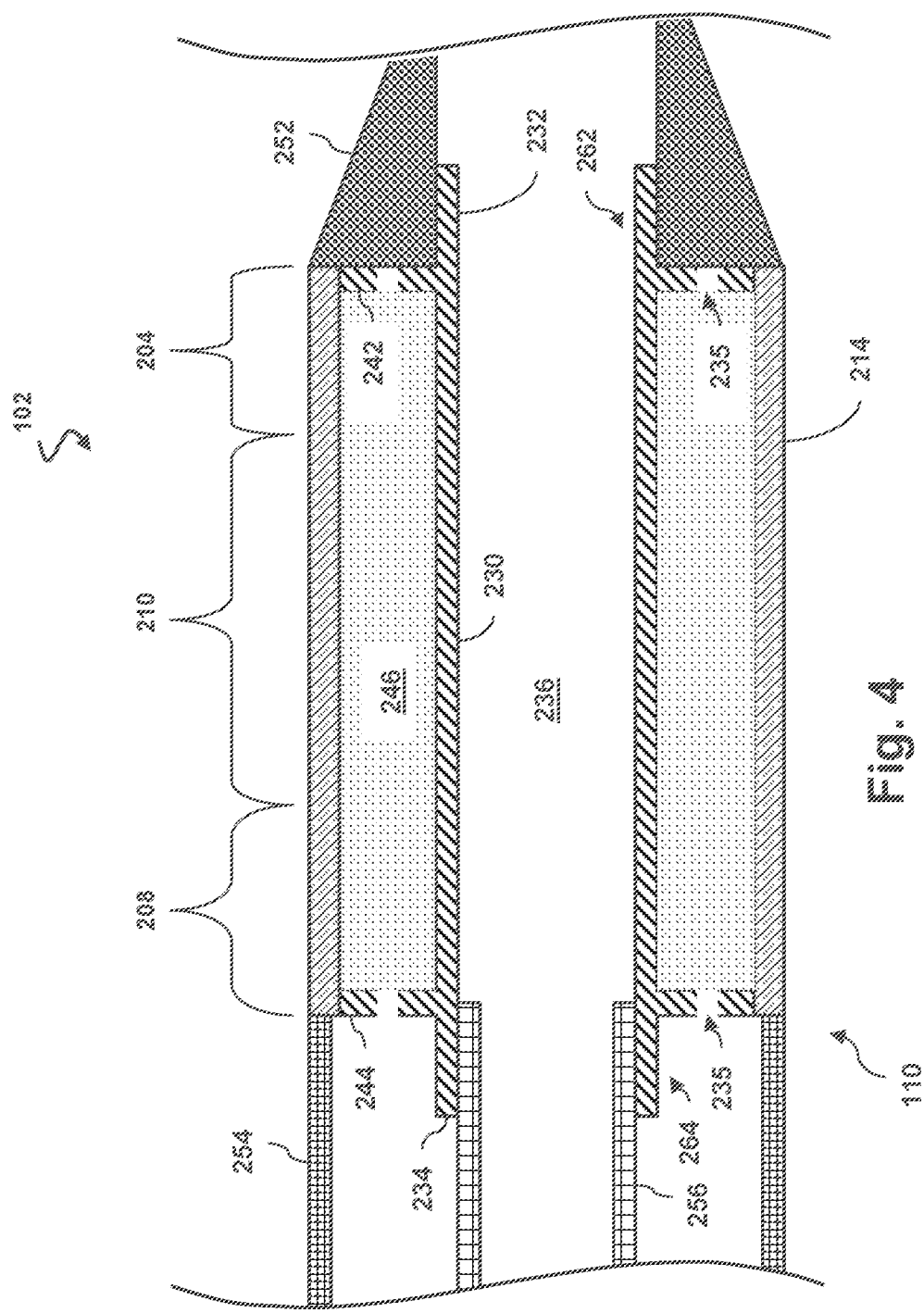
FIG. 4 is a diagrammatic cross-sectional side view of a distal portion of an intravascular device, according to aspects of the present disclosure.

In some instances, the scanner assembly 110 is transitioned from a flat configuration (FIG. 2) to a rolled or more cylindrical configuration (FIGS. 3 and 4). For example, in some embodiments, techniques are utilized as disclosed in one or more of U.S. Pat. No. 6,776,763, titled "ULTRASONIC TRANSDUCER ARRAY AND METHOD OF MANUFACTURING THE SAME" and U.S. Pat. No. 7,226, 417, titled "HIGH RESOLUTION INTRAVASCULAR ULTRASOUND TRANSDUCER ASSEMBLY HAVING A FLEXIBLE SUBSTRATE," each of which is hereby incorporated by reference in its entirety.

As shown in FIGS. 3 and 4, the flex circuit 214 is positioned around the support member 230 in the rolled configuration. FIG. 3 is a diagrammatic side view with the flex circuit 214 in the rolled configuration around the support member 230, according to aspects of the present disclosure. FIG. 4 is a diagrammatic cross-sectional side view of a distal portion of the intravascular device 110, including the flex circuit 214 and the support member 230, according to aspects of the present disclosure.

The support member 230 can be referenced as a unibody in some instances. The support member 230 can be composed of a metallic material, such as stainless steel, or non-metallic material, such as a plastic or polymer as described in U.S. Provisional Application No. 61/985,220, "Pre-Doped Solid Substrate for Intravascular Devices," filed Apr. 28, 2014, the entirety of which is hereby incorporated by reference herein. The support member 230 can be ferrule having a distal portion 262 and a proximal portion 264. The support member 230 can define a lumen 236 extending longitudinally therethrough. The lumen 236 is in communication with the exit port 116 and is sized and shaped to receive the guide wire 118 (FIG. 1). The support member 230 can be manufactured accordingly to any suitable process. For example, the support member 230 can be machined, such as by removing material from a blank to shape the support member 230, or molded, such as by an injection molding process. In some embodiments, the support member 230 may be integrally formed as a unitary structure, while in other embodiments the support member 230 may be formed of different components, such as a ferrule and stands 242, 244, that are fixedly coupled to one another.

Stands 242, 244 that extend vertically are provided at the distal and proximal portions 262, 264, respectively, of the support member 230. The stands 242, 244 elevate and support the distal and proximal portions of the flex circuit 214. In that regard, portions of the flex circuit 214, such as the transducer portion 204, can be spaced from a central body portion of the support member 230 extending between the stands 242, 244. The stands 242, 244 can have the same outer diameter or different outer diameters. For example, the distal stand 242 can have a larger or smaller outer diameter than the proximal stand 244. To improve acoustic performance, any cavities between the flex circuit 214 and the surface of the support member 230 are filled with a backing material 246. The liquid backing material 246 can be introduced between the flex circuit 214 and the support member 230 via passageways 235 in the stands 242, 244. In some embodiments, suction can be applied via the passageways 235 of one of the stands 242, 244, while the liquid backing material 246 is fed between the flex circuit 214 and the support member 230 via the passageways 235 of the other of the stands 242, 244. The backing material can be cured to allow it to solidify and set. In various embodiments, the support member 230 includes more than two stands 242, 244, only one of the stands 242, 244, or neither of the stands. In that regard the support member 230 can have an increased diameter distal portion 262 and/or increased diameter proximal portion 264 that is sized and shaped to elevate and support the distal and/or proximal portions of the flex circuit 214.

The support member 230 can be substantially cylindrical in some embodiments. Other shapes of the support member 230 are also contemplated including geometrical, non-geometrical, symmetrical, non-symmetrical, cross-sectional profiles. Different portions the support member 230 can be variously shaped in other embodiments. For example, the proximal portion 264 can have a larger outer diameter than the outer diameters of the distal portion 262 or a central portion extending between the distal and proximal portions 262, 264. In some embodiments, an inner diameter of the support member 230 (e.g., the diameter of the lumen 236) can correspondingly increase or decrease as the outer diameter changes. In other embodiments, the inner diameter of the support member 230 remains the same despite variations in the outer diameter.

A proximal inner member 256 and a proximal outer member 254 are coupled to the proximal portion 264 of the support member 230. The proximal inner member 256 and/or the proximal outer member 254 can be flexible elongate member that extend from proximal portion of the intravascular device 102, such as the proximal connector 114, to the imaging assembly 110. For example, the proximal inner member 256 can be received within a proximal flange 234. The proximal outer member 254 abuts and is in contact with the flex circuit 214. A distal member 252 is coupled to the distal portion 262 of the support member 230. The distal member 252 can be a flexible component that defines a distal most portion of the intravascular device 102. For example, the distal member 252 is positioned around the distal flange 232. The distal member 252 can abut and be in contact with the flex circuit 214 and the stand 242. The distal member 252 can be the distal-most component of the intravascular device 102.

One or more adhesives can be disposed between various components at the distal portion of the intravascular device 102. For example, one or more of the flex circuit 214, the support member 230, the distal member 252, the proximal inner member 256, and/or the proximal outer member 254 can be coupled to one another via an adhesive.

Figure 5:
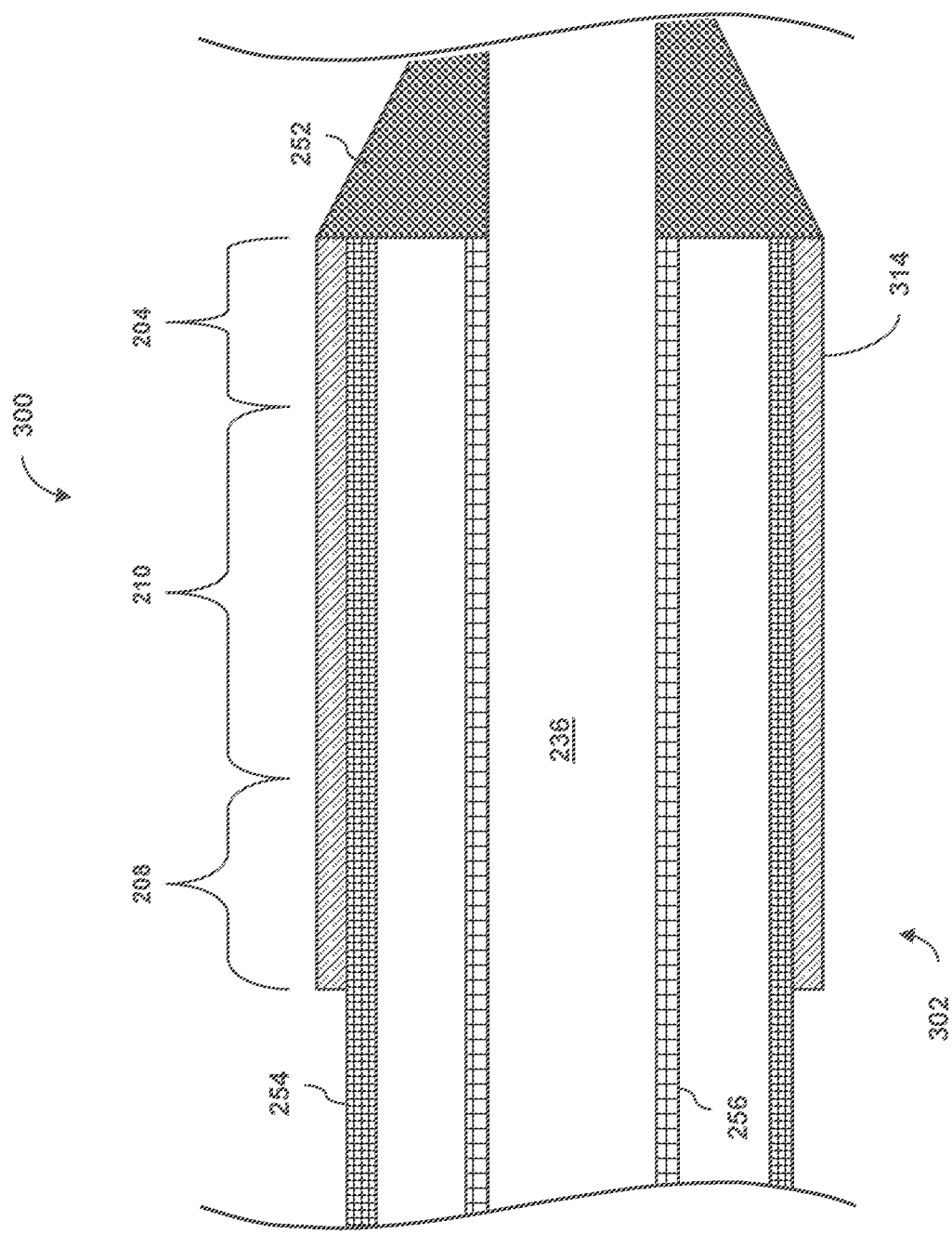
FIG. 5 is a diagrammatic cross-sectional side view of a distal portion of an intravascular device, according to aspects of the present disclosure.

FIG. 5 is diagrammatic cross-sectional side view an embodiment of an intravascular device 300, including an imaging assembly 302. The intravascular device 300 and the imaging assembly 302 may be similar to the intravascular device 102 and the imaging assembly 110, in some aspects.

A flex circuit 314 of the imaging assembly 302 is positioned directly around the proximal member 254. For example, the flex circuit 314 may be rolled into a cylindrical or cylindrical toroid configuration around the proximal member 254. The imaging assembly 302 does not include a uni-body or support structure. By omitting the rigid support structure from the imaging assembly 302, distal portion of the intravascular device 300 is advantageously more flexible. For example, the components at the distal portion of the intravascular device 300, including the flex circuit 314, the proximal members 254, 256, and the distal member 252, are formed of flexible materials. Accordingly, the intravascular device 3000 may more easily traverse tortuous physiology within a patient's body.

In the embodiments of FIG. 5, the flex circuit 314 is positioned directly around the outer member 254. In some embodiments, the intravascular device 300 includes only one proximal member. In such embodiments, the flex circuit 314 can be positioned directly around the one proximal member.

Figure 6:
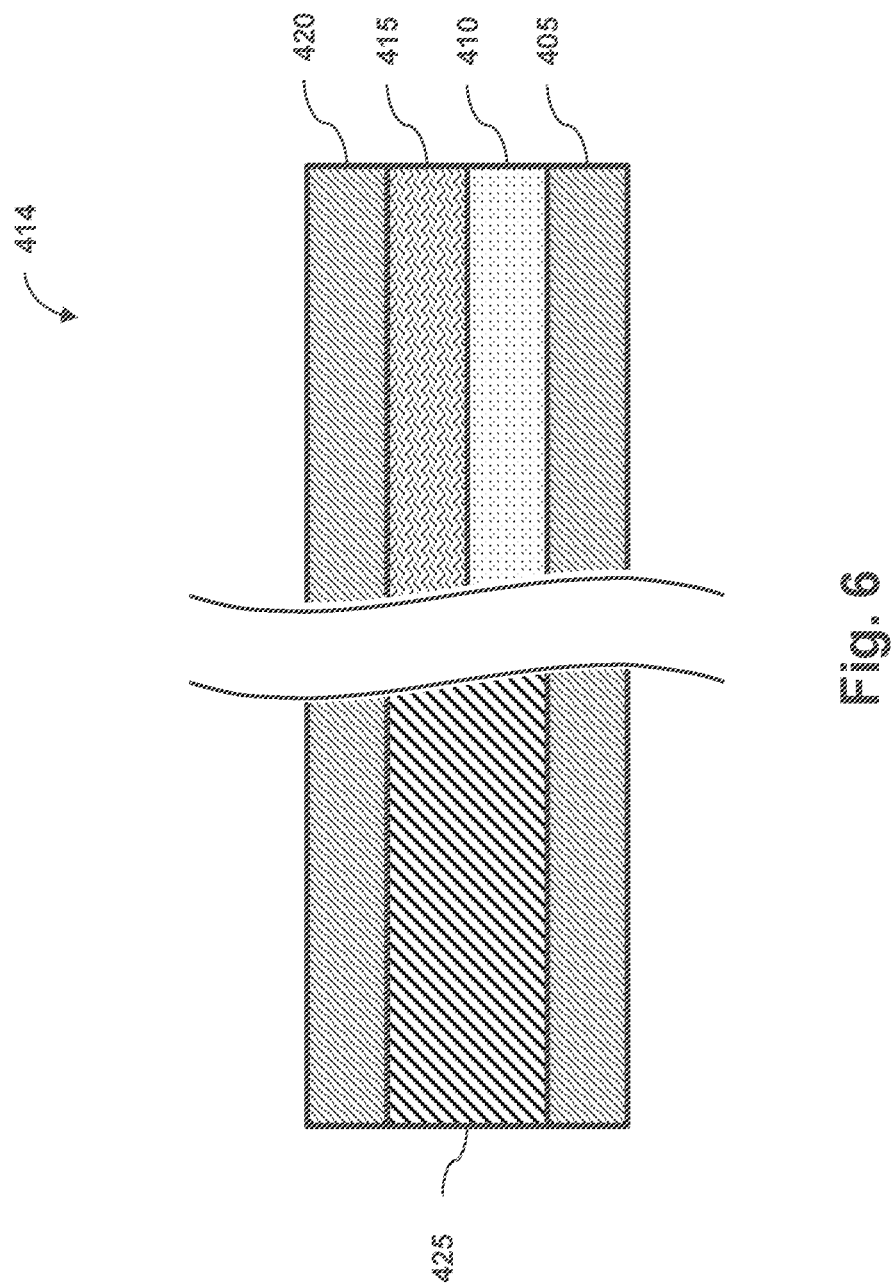
FIG. 6 is a diagrammatic cross-sectional side view of a flex circuit, according to aspects of the present disclosure.

FIG. 6 is a diagrammatic cross-sectional side of an embodiment of a flex circuit 414. The flex circuit 414 can be wrapped directly around the proximal member 254. FIG. 6 illustrates layers of the flex circuit 414. In that regard, the flex circuit 414 includes a layer 415 in which the plurality of transducers 212 are positioned. For example, the transducers 212 can be formed within the layer 415 according to any suitable manufacturing technique(s), such as those described in U.S. Provisional App. No. 61/746,804, titled "Intravascular Ultrasound Imaging Apparatus, Interface, Architecture, and Method of Manufacturing," and filed Dec. 28, 2012, the entirety of which is hereby incorporated by reference herein. In some embodiments, the layer 415 is between approximately 50 μm and approximately 200 μm.

The layer 415 is positioned over a layer 410 including an acoustic backing material. The backing material facilitates operation of the transducers 212 by improving acoustic performance. The acoustic backing material can include one or more of cerium oxide, an epoxy such as EPO-TEK, a mix containing filler/additive materials such as tungsten, polymethylpentene, crosslinked polystyrene, and/other suitable materials etc. The backing material may contain one or more fillers such as tungsten, polymethylpentene, crosslinked polystyrene. In some embodiments, the layer 415 of transducers can be positioned over multiple backing layers which together satisfy the acoustic requirements of the transducers. The acoustic backing material may be formed on the layer 410 using any suitable technique, including physical vapor deposition, chemical vapor deposition, chemical adsorption, physical adsorption, dip coating, solvent evaporation, etc. In some embodiments, the layer 410 is between approximately 50 μm and approximately 200 μm.

The layer 410 can be positioned on the flexible substrate 405. A flex substrate layer 420 can also be positioned over the layer 415. The flexible substrates 405, 420 provide structural integrity and flexibility to the flex circuit 414. The flexible substrates 405, 220 can be a film layer of a flexible polyimide material such as KAPTON™ (trademark of DuPont). Other suitable materials include polyester films, polyimide films, polyethylene napthalate films, or polyetherimide films, other flexible printed semiconductor substrates as well as products such as Upilex® (registered trademark of Ube Industries) and TEFLON® (registered trademark of E.I. du Pont). In some embodiments, each of the layers 405, 420 is between approximately 1 μm and approximately 100 μm. The layer 405 may be in contact with the proximal member 254 when the flex circuit 414 is wrapped around the proximal member 254.

The flex circuit 414 can also include a layer 425 including a plurality of controllers (e.g., the controllers 206A, 206B). For example, the controllers can be formed within the layer 425 according to any suitable technique, such as those described in U.S. Provisional App. No. 61/746,804, titled "Intravascular Ultrasound Imaging Apparatus, Interface, Architecture, and Method of Manufacturing," and filed Dec. 28, 2012, the entirety of which is hereby incorporated by reference herein. The plurality of controllers of layer 425 is in electrical communication with the plurality of transducers 212 of layer 415. In that regard, conductive traces and/or electrical interconnects can be formed within the layers 415, 425. In some embodiments, the flex circuit 414 includes an additional layer including electrical interconnects establishing electrically communication between controllers and transducers.

In some embodiments, the flex circuit 414 can have a transducer segment and controller segment. For example, the transducer segment can include the layers 405, 410, 415, and 420. The controller segment can include the layers 405, 425, and 420. The transducer segment and the controller segment can be spaced from one another. For example, a flexible substrate layer can extend longitudinally between the two segments. This flexible substrate layer can include conductive traces establishing electrical communication between the controllers and the transducers. In some embodiments, one of the transducer segment and the controller segment may be implemented without a support member or uni-body structure in the intravascular device 102, while the other of the transducer segment and the controller is implemented with a support member or uni-body structure. For example, the transducer segment may be wrapped around a support member including stands that elevate the transducer segment from a main body of the support member. The space between the transducer segment and the support member may be filled with an acoustic backing material. The controller segment may be implemented without a support member such that the controller segment is wrapped directly around the outer proximal member. Some exemplary arrangements are described in U.S. Provisional App. No. 62/315,406, filed on Mar. 30, 2016, the entirety of which is hereby incorporated by reference herein.

Figure 7:
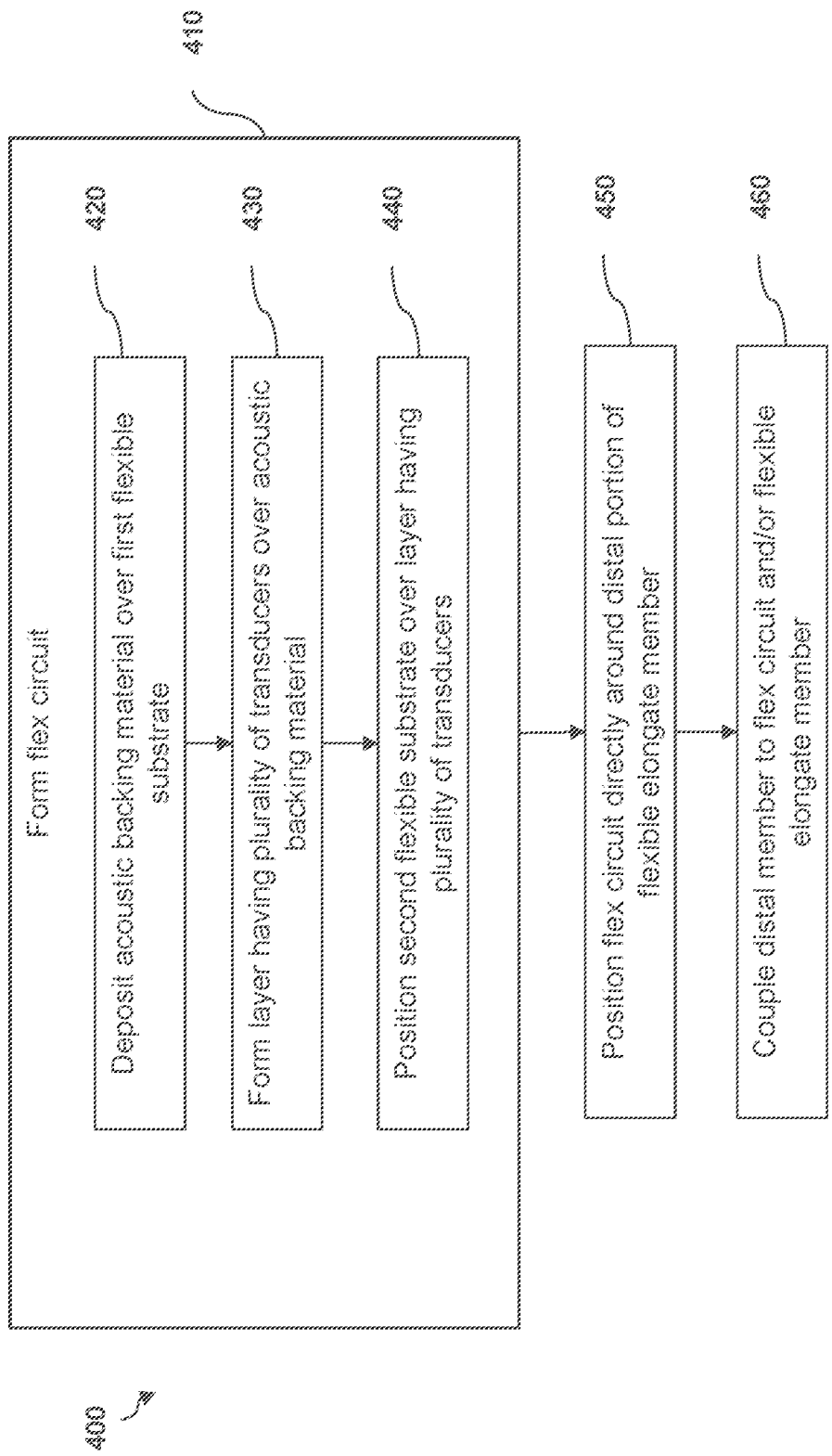
FIG. 7 is a flow diagram of a method of assembling an intravascular device, according to aspects of the present disclosure.

FIG. 7 is a flow diagram of a method 400 of assembling an intravascular imaging device, including an imaging assembly with a support member described herein. It is understood that the steps of method 400 may be performed in a different order than shown in FIG. 7, additional steps can be provided before, during, and after the steps, and/or some of the steps described can be replaced or eliminated in other embodiments. The steps of the method 400 can be carried out by a manufacturer of the intravascular imaging device.

At step 410, the method 400 includes forming a flex circuit. The flex circuit includes electronic components, such as a plurality of transducers and a plural of controllers, of an imaging assembly. Forming the flex circuit can include, at step 420, depositing an acoustic backing material over a first flexible substrate. At step 430, forming the flex circuit can include forming a layer having the plurality of transducers over the acoustic backing material. At step 440, forming the flex circuit can include position a second flexible substrate over the layer having the plurality of transducers. In some embodiments, forming the flex circuit can additionally include forming a plurality of controllers in a layer of the flex circuit. In some embodiments, the plurality of controllers can be formed in the same layer as the plurality of transducers. Forming the flex circuit can also include disposing conductive traces facilitating electrical communication between the transducers and controllers onto one or more layers of the flex circuit. In some embodiments, forming the flex circuit can include forming an interconnect layer to establish electrical communication between the transducers and controllers.

At step 450, the method 440 includes positioning the flex circuit directly around a distal portion of a flexible elongate member. In that regard, the flex circuit may be formed (step 410-440) with the flex circuit in a planar configuration. Step 450 can include transitioning the flex circuit into a cylindrical or cylindrical toroid configuration, such as by wrapping, around the flexible elongate member. For example, the flexible elongate member can be an outer proximal member.

At step 460, the method 400 includes include coupling the flex circuit and/or flexible elongate member to a distal member that defines a distal-most end of the intravascular imaging device. The method 400 can include introducing adhesive to affix the flex circuit, the flexible elongate member, the distal member, and/or other components of the intravascular imaging device.

The method 400 can additionally include electrically coupling a conductor the flex circuit. The intravascular device can include a plurality of conductors. The method 400 can also include positioning the one or more conductors within a flexible elongate member. The conductor(s) can extend along a length of the intravascular device. The conductor(s) can be threaded through the flex elongate member such that, e.g., the conductor(s) are positioned with a lumen of an outer member and/or disposed between an inner member and an outer member.

Various embodiments of an intravascular device and/or imaging assembly can include features described in U.S. Provisional App. No. 62/315,395, filed on Mar. 30, 2016, U.S. Provisional App. No. 62/315,406, filed on Mar. 30, 2016, U.S. Provisional App. No. 62/315,421, filed on Mar. 30, 2016, and U.S. Provisional App. No. 62/315,428, filed on Mar. 30, 2016, the entireties of which are hereby incorporated by reference herein.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An apparatus, comprising:
   an intravascular imaging catheter comprising:
   a flexible elongate member sized and shaped for insertion into a vessel of a patient, wherein the flexible elongate member comprises:
   an outer member comprising:
   a distal portion terminating at a distal end; and
   an outer surface;
   an inner member positioned inside the outer member; and
   a flex circuit positioned at the distal portion of the flexible elongate member,
   wherein the flex circuit comprises a distal portion with a plurality of transducers and a proximal portion with a plurality of controllers in communication with the plurality of transducers,
   wherein the flex circuit is positioned directly around the outer surface of the outer member such that the plurality of transducers is positioned proximate to the distal end of the outer member.

2. The apparatus of claim 1, wherein the distal portion of the flex circuit terminates at a distal end, wherein the distal end of the flex circuit is aligned with the distal end of the outer member.

3. The apparatus of claim 1,
   wherein the inner member comprises a distal portion terminating at a distal end,
   wherein the distal end of the inner member is aligned with the distal end of the outer member.

4. The apparatus of claim 1, wherein the flex circuit comprises a plurality of conductive traces configured to provide the communication between the plurality of controllers and the plurality of transducers.

5. The apparatus of claim 1, wherein an entire length of the flex circuit is positioned outside of the outer member such that the plurality of transducers and the plurality of controllers are positioned outside of the outer member.

6. The apparatus of claim 1,
wherein the flex circuit comprises an inner surface,
wherein the outer surface of the outer member faces the inner surface of the flex circuit.

7. The apparatus of claim 6, wherein the inner surface of the flex circuit directly contacts the outer surface of the outer member.

8. The apparatus of claim 1, wherein the flex circuit encircles the outer member.

9. The apparatus of claim 1, wherein the flex circuit is an outermost component of the intravascular imaging catheter at the distal portion of the outer member.

10. The apparatus of claim 1, wherein the outer member is an outermost component of the intravascular imaging catheter proximal of the flex circuit.

11. The apparatus of claim 1,
wherein the intravascular imaging catheter further comprises a distal member comprising a proximal end,
wherein the distal member is a distal-most component of the intravascular imaging catheter,
wherein the proximal end of the distal member is immediately adjacent to the distal end of the outer member.

* * * * *